United States Patent [19]

Slusarchyk et al.

[11] 4,029,645
[45] June 14, 1977

[54] MERCURY INTERMEDIATES USEFUL IN THE PREPARATION OF 2-ALKOXY CEPHALOSPORINS

[75] Inventors: William A. Slusarchyk, Belle Mead; Christopher M. Cimarusti, Hamilton, both of N.J.

[73] Assignee: E. R. Squibb & Sons, Inc., Princeton, N.J.

[22] Filed: Nov. 17, 1975

[21] Appl. No.: 632,617

[52] U.S. Cl. .................. 260/239 A; 260/270 K; 260/299; 260/326 E; 260/326.22; 260/332.2 H; 260/347.2
[51] Int. Cl.² ................................. C07D 205/08
[58] Field of Search ...... 260/239 A, 326 E, 326.22, 260/299, 270 K, 332.41, 347.2

[56] References Cited

UNITED STATES PATENTS 3,090,788   5/1963   Hoffer et al. .................... 260/299

OTHER PUBLICATIONS

Goodhue et al., Chem. Abs. 54, 21140a, (1960).
Haning et al., Am. J. Chem. 52, 2950–2952, (1974).
Schuetz, et al., J. Org. Chem. 27, 1301–1304, (1962).
Prout et al., J.A.C.S. 75, 4057–4058, (1953).
Lattrell, Am. Chem., 1974, 1361–1390.
Lattrell et al., Chem. Abs. 80, 95703v, (1974).
Bach et al., Chem. Abs. 76, 33846c, (1972).
H. C. Brown et al., J. Amer. Chem., 50091, 5646–5647.
Nosmeyanova et al., Chem. Abs., 60, 5303, (1963).
Albrecht et al., J. Organomet, Chem., 57, 77–86, (1973).
Indian J. Chem. 12, 781–783, (1974), (Behura et al.).
Poutsina et al., J. Amer. Chem. Soc. 93, 440–450, (1971).

Primary Examiner—Donald G. Daus
Assistant Examiner—Mark L. Berch

Attorney, Agent, or Firm—Lawrence S. Levinson; Merle J. Smith; Stephen B. Davis

[57] ABSTRACT

Compounds of the formula

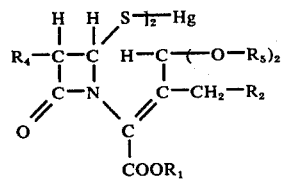

wherein $R_1$ is lower alkyl, diphenylmethyl, 2,2,2-trichloro-ethyl, p-methoxybenzyl, or p-nitrobenzyl; $R_2$ is hydrogen or acetoxy; $R_5$ is lower alkyl; and $R_4$ is

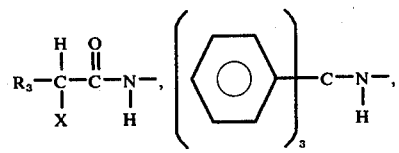

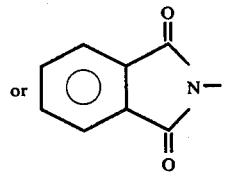

wherein $R_3$ is a heterocyclic group, lower alkyl, cycloalkyl, cycloalkenyl, cycloalkadienyl, phenyl, substituted phenyl, phenyl-lower alkyl, or phenoxy and X is hydrogen, protected amino or protected hydroxy provided that X is protected amino or protected hydroxy only when $R_3$ is phenyl, substituted phenyl, or cycloalkadienyl, are disclosed. These compounds are useful as intermediates in the preparation of antibacterially active 2-alkoxy cephalosporins.

9 Claims, No Drawings

MERCURY INTERMEDIATES USEFUL IN THE PREPARATION OF 2-ALKOXY CEPHALOSPORINS

BACKGROUND OF THE INVENTION

2-Alkoxy cephalosporins are disclosed as possessing antibacterial activity in U.S. Pat. No. 3,852,282 to Dolfini, by spry, Tetrahedron Letters No. 35, p. 3717–3720 (1972), and Netherlands Pat. No. 7,308,544.

SUMMARY OF THE INVENTION

This invention relates to new compounds of the formula

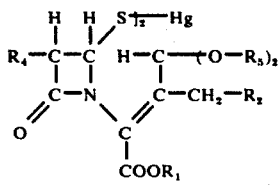

wherein $R_1$ is lower alkyl, diphenylmethyl, 2,2,2-trichloroethyl, p-methoxybenzyl, or p-nitrobenzyl; $R_2$ is hydrogen or acetoxy; $R_5$ is lower alkyl; and $R_4$ is

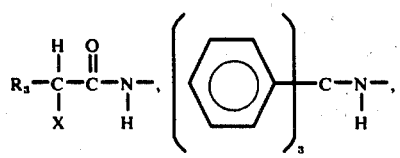

or

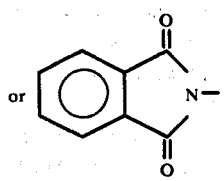

wherein X is hydrogen, protected amino, or protected hydroxy and $R_3$ represents certain heterocyclic groups, lower alkyl, cycloalkyl, cycloalkenyl, cycloaladienyl, phenyl, phenoxy, phenyl-lower alkyl, or substituted phenyl provided that X is protected amino or protected hydroxy only when $R_3$ is phenyl, substituted phenyl, or cycloalkadienyl.

The esters of formula I are useful as intermediates in the preparation of cephalosporins possessing antibacterial activity.

DETAILED DESCRIPTION

The various groups represented by the symbols have the meaning defined below and these definitions are retained throughout this specification.

The term "lower alkyl" is intended to include straight or branched chain hydrocarbon groups containing 1 to 4 carbons, i.e. methyl, ethyl, n-propyl, i-propyl, t-butyl, etc. The term "phenyl-lower alkyl" includes such lower alkyl groups attached to a phenyl with benzyl and phenethyl being preferred. The "lower alkoxy" groups include such lower alkyl groups attached to an oxygen, i.e. methoxy, ethoxy, etc.

"Cycloalkyl" refers to groups having 3 to 7 carbons in the ring, i.e. cyclopropyl, cyclobutyl, cyclopentyl, cyclohexyl, and cycloheptyl. The term "cycloalkenyl" also represents rings having 3 to 7 carbons with one double bond, i.e. cyclobutenyl, cyclopentenyl, cyclohexenyl, etc. The term "cycloalkadienyl" represents a ring having 6 or 7 carbons with two double bonds located at various positions such as 1,4-cyclohexadienyl which is preferred.

The terms "protected amino" and "protected hydroxy" include groups which can be removed during the last step of the reaction procedure to yield the free amino or free hydroxy compound but will not be removed during the initial reaction steps. Such groups are well known in the cephalosporin art. For example,

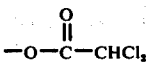

is a protected hydroxy group which can be removed by treatment with sodium carbonate at a pG of about 9.5 to yield the free hydroxy compound. Similarly,

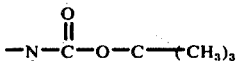

and

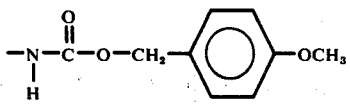

are protected amino compounds which can be removed by treatment with trifluoroacetic acid to yield the free amino compound.

The "substituted phenyl" groups include one or two simple substituents such as halogen (preferably Cl or Br), lower alkyl, or lower alkoxy, i.e. 2-, 3-, or 4-chlorophenyl, 2-, 3, or 4-bromophenyl, 3,5-dichlorophenyl, 2-, 3-, or 4chlorophenyl, 2-, 3-, or 4-bromophenyl, 3,5-dichlorophenyl, 2-, 3-, or 4-methylphenyl, 2-, 3, or 4-methoxyphenyl, etc.

The heterocyclics represented by $R_3$ are thienyl, furyl, pyrryl, pyridyl, thiazolyl, isothiazolyl, oxazolyl, isoaxazolyl, thiadiazolyl, and tetrazolyl. They are attached at any available carbon atom as for example 2- or 3-thienyl, 2- or 3-furyl, 2- or 3-pyrryl, 2-, 3-, or 4-pyridyl, 2- or 5-thiazolyl, 3- or 5-isothiazolyl, 2-or 5-oxazolyl, 3- or 5-isoxazolyl, 3- or 5-(1,2,4-thiadiazolyl), etc. Also included within the meaning of $R_3$ are such heterocyclics having a halogen (preferably Cl or Br) or a lower alkyl (preferably methyl or ethyl) substituent, i.e. 5-(1-methyltetrazolyl), 2-(5-chlorothienyl), 2-(4-chloropyrryl), etc.

The esters of formula I are useful as intermediates in the preparation of 2-alkoxy substituted cephalosporins of the formula

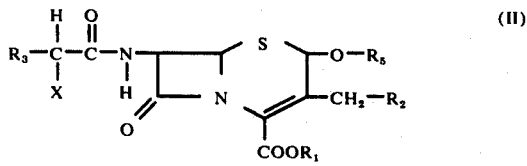

wherein $R_1$, $R_2$, $R_3$, $R_5$, and X are as defined above. The esters of formula II can then be reacted to yield the corresponding acid compound and to remove the α-amino or α-hydroxy protecting group according to methods well known in cephalosporin art.

The compounds of formula I wherein $R_4$ is

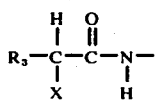

are converted to cephalosporins of formula II by treatment with excess hydrogen sulfide in an inert organic solvent such as dichloromethane, chloroform, 1,2-dichloroethane, dimethoxyethane, dioxane, tetrahydrofuran or benzene at a temperature of from about −40° C to 40° C for from about 2 minutes to about one hour. Also, the alkoxy substituent in the 2-position of the formula II compound can be changed in this process by performing the reaction in the presence of an excess of alcohol ($HO-R_5$) wherein the $R_5$ group is different from that in formula I.

The compounds of formula I wherein $R_4$ is

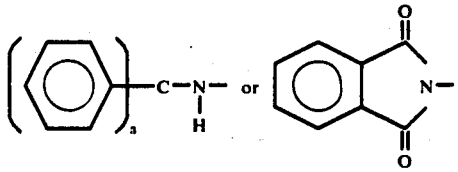

when treated with hydrogen sulfide as set forth above yield the intermediates of the formula

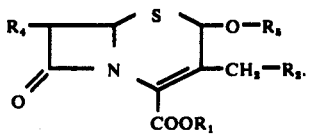  (III)

When $R_4$ is

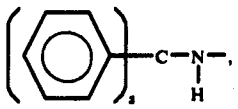

the intermediate of formula III is hydrolyzed with an acid such as p-toluenesulfonic acid, hydrochloric acid, sulfuric acid, or perchloric acid to yield the 7-amino-2-alkoxy-cephalosporin of the formula

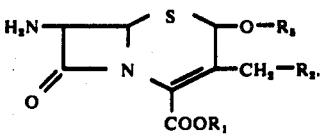  (IV)

Similarly, when $R_4$ is

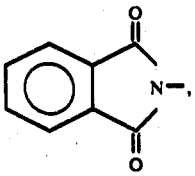

the intermediate of formula III can be converted to the 7-amino-2-alkoxy-cephalosporin of formula IV by known methods such as that taught by Kukolja et al. in the Journal of the Amer. Chem. Society, Vol. 97, p. 5582–5583. The 7-amino compound of formula IV can then be acylated with an acyl halide,

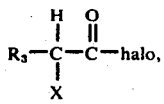

as taught in Netherlands Pat. No. 7,308,544, to yield the compound of formula II.

The compounds of formula I are prepared by treating a $\Delta^3$-cephem of formula

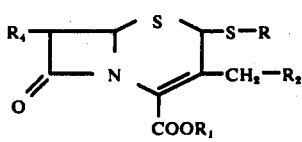  (V)

or a $\Delta^2$-cephem of formula

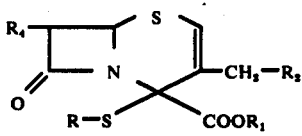  (VI)

wherein $R_1$, $R_2$ and $R_4$ are as defined above and R is lower alkyl or phenyl, with one to two equivalents of mercuric acetate and an alcohol ($HO-R_5$) in an inert organic solvent such as dimethoxyethane, dioxane, tetrahydrofuran, benzene acetonitrile, or the alcohol itself could be employed as the solvent, at a temperature of from about 0° C to about 80° C for from about 5 minutes to about 2 hours.

The preparation of some of the starting materials of formula V (e.g. the compounds wherein $R_4$ is

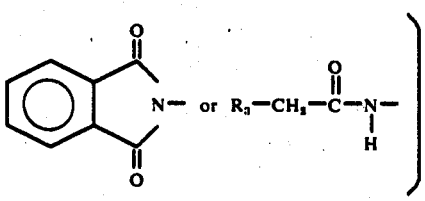

are disclosed in U.S. Pat. No. 3,852,282. The preparation of the starting materials of formulas V and VI wherein $R_4$ is

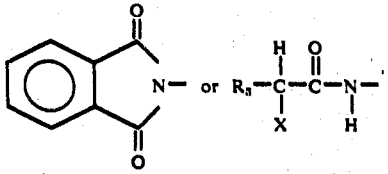

are taught in German Offenlegungsschrift Nos. 2,453,601 and 2,455,358.

The starting materials of formula VI wherein $R_4$ is

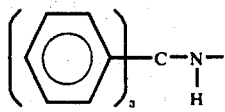

are prepared by reacting an ester of the formula

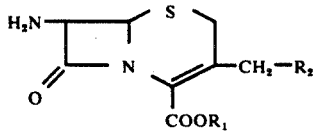
(VII)

with triphenylmethyl chloride in the presence of triethylamine in an inert solvent such as $CH_2Cl_2$ to yield the compound of formula

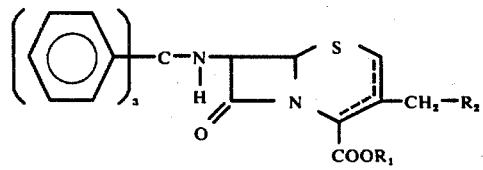
(VIII)

wherein the dashed line indicates that the double bond may be in either the 2- or 3-position. The compound of formula VIII is then treated with one to two equivalents of a strong organometallic base such as potassium t-butoxide, n-butyl lithium, triphenylmethyl lithium, lithium N-cyclohexylisopropyl amide, lithium diethylamide or lithium hexamethyldisilazane, followed by a thiolating agent to yield the starting material of formula VI wherein $R_4$ is

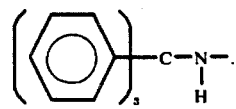

The thiolating agent can be any of a varied group of agents known to introduce a substituted sulfur such as a compound of the formula

R—S—Y (IX)

wherein Y is halogen (preferably Cl or Br), lower alkoxycarbonyl (preferably methoxycarbonyl), or a sulfonic acid ester, e.g. $-SO_2-Z$ wherein Z is lower alkyl, phenyl, or substituted phenyl; or a disulfide thiolating agent of the formula (R-S)$_2$ (X)

wherein R is as defined above. About one equivalent or more of the thiolating agent is used. This reaction is performed in an inert organic solvent such as dimethoxyethane, dimethylformamide, tetrahydrofuran, dimethylsulfoxide, dioxane, or the like, at a temperature range of from about $-70°$ C to about $30°$ C for from several minutes to several hours. The reaction is best carried out under an inert atmosphere, e.g. argon or nitrogen.

The starting materials of formula V wherein $R_4$ is

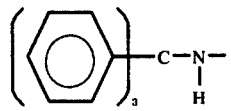

are prepared by treating the starting material of formula VI wherein $R_4$ is

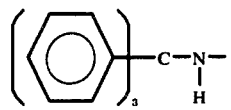

with mercuric acetate at room temperature in an organic solvent such as dimethoxyethane.

As stated in U.S. Pat. No. 3,852,282, the compounds of formula II especially in the acid form are useful against gram-positive bacteria, such as *Staphylococcus aureus* and *Streptococcus pyogenes*. These compounds may be used to combat infections due to organisms such as those named above, and in general may be formulated and administered in a manner similar to cephalothin and other cephalosporins. For example, these compounds of formula II or a physiologically acceptable salt thereof may be used in various animal species in an amount of from about 1 to about 100 mg./kg., daily, orally or parenterally, in single or two to four divided doses to treat infections of bacterial origin, e.g. 5 mg./kg. in mice. Up to about 600 mg. of an acid compound of formula II or a physiologically acceptable salt thereof may be incorporated in an oral dosage form such as tablets, capsules, or elixirs, or in an injectable form in a sterile aqueous vehicle prepared according to conventional pharmaceutical practice.

The following examples represent preferred embodiments of this invention. All temperatures are on the centigrade scale.

EXAMPLE 1

2-Methoxy-3-methyl-7-phenylacetylamino-$\Delta^3$-cephem-4-carboxylic acid, 2,2,2-trichloroethyl ester a. Bis[[1-[(2,2,2-trichloroethoxy)carbonyl]-2-methyl-3,3-dimethoxy-1-propenyl]-3-[ ]phenylacetyl)amino]-4-oxo-2-azetidinyl]thio]mercury A mixture of 1.96 mmol. of 4-methylthio-7-phenylacetamido-3-methyl-$\Delta^2$-cephem-4-carboxylic acid,2,2,2-trichloroethyl ester (prepared as taught in German Offenlegungsschrift No. 2,453,601) and 1.96 mmol. of mercuric acetate in 10 ml. of dry methanol is stirred at 25° C under nitrogen for 30 minutes. The solvent is removed in vacuo, and the residue is treated with $CHCl_3$ and water. The $CHCl_3$ layer is washed with water three times, dried ($Na_2SO_4$), and evaporated to a residue. The residue is purified by thin layer chromatography on silica gel in the system $CHCl_3$:EtOAc (9:1), and the desired product is obtained as an amorphous residue (282 mg.) having the following spectral properties: pmr (DCCl$_3$) Δ 4.27 (1H,d, J=5Hz,C-2), 4.62, 4.77 (1H,q,J=5Hz,J=8Hz,C-3), 5.00 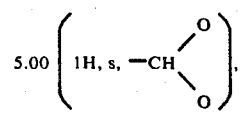

6.57 (3H,s,—OCH₃), 6.60 (3H,s,—OCH₃); ir (CHCl₃,cm⁻¹) 1775, 1755 (sh), 1685.

b. 2-Methoxy-3-methyl-7-phenylacetylamino-Δ³-cephem-4-carboxylic acid,2,2,2-trichloroethyl ester One gram of the mercury compound from part (a) in 50 ml. of dry dichloromethane is treated by bubbling hydrogen sulfide through the solution for 15 minutes at 25° C, with the reaction being protected from atmospheric moisture. The reaction mixture is filtered through "Celite", and the filtrate is evaporated to a residue which is taken up in benzene and water. The benzene layer is washed with water, dried (Na₂SO₄), and evaporated to a residue (641 mg.). This residue is purified by thin layer chromatography on silica gel in the system CHCl₃—EtOAc (4:1) to give a faster moving component (266 mg.), 2α -methoxy-3-methyl-7-phenylacetylamino-Δ³-cephem-4-carboxylic acid, 2,2,2-trichloroethyl ester and a slower moving component (129 mg.), 2β -methoxy-3-methyl-7-phenylacetylamino-Δ³-cephem-4-carboxylic acid, 2,2,2-trichloroethyl ester. The 2α -methoxy ester has: pmr (DCCl₃) τ 7.78 (3H,s,C-3 methyl), 6.52 (3H,s, —OCH₃) 4.97, 5.22 (2H,q,J=13Hz,—OCH₂CCl₃), 5.18 (1H,d,J=0.5Hz, C-2), 4.97 (1H,d,J=5Hz,C-6), 4.00, 4.15 (1H,q,J=5Hz,J=9H,C-7); m.p. 133.5°-134° (acetone-hexane).

Calculated for C₁₉H₁₉O₅N₂SCl₃: C, 46.21; H, 3.88; N, 5.67; S, 6.49. Found: C, 46.47; H, 4.00; N, 5.49; S, 6.36.

The β-methoxy ester has: pmr (DCCl₃) τ 7.60 (3H,s,C-3 methyl), 7.03 (3H,s,—OCH₃), 5.40 (1H,s,C-2), 5.13 (2H,s,—OCH₂—CCl₃), 4.80 (1H,d,J=4-Hz,C-6), 4.15, 4.30 (1H,q,J=4Hz,J=10Hz, C-7); ir (CHCl₃) 1790, 1738, and 1675; mass spectrum 492 (M⁺).

EXAMPLE 2

2-Ethoxy-3-methyl-7-phenylacetylamino-Δ³-cephem-4-carboxylic acid, methyl ester and 2-methoxy-3-methyl-7-phenylacetylamino-Δ³-cephem-4-carboxylic acid, methyl ester a. Bis[[1-[1-[(methoxy)carbonyl]-2-methyl-3,3-dimethoxy-1-propenyl]-3-[(phenylacetyl)amino]-4-oxo-2-azetidinyl]thio]mercury Following the procedure of example 1(a) but substituting an equivalent amount of 4-methylthio-7-phenylacetamido-3-methyl-Δ²-cephem-4-carboxylic acid, methyl ester for the 2,2,2-trichloroethyl ester, one obtains the titled compound having the following spectral properties: pmr (DCCl₃) τ 4.35 (1H,d,J=5Hz, C-2), 4.63, 4.73 (1H,q,J=5Hz,J 8Hz,C-3) 5.08

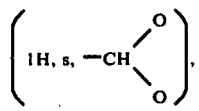

6.62 (6H,s,—OCH₃); ir (CHCl₃, cm⁻¹) 1770, 1730, 1685.

b. 2Ethoxy-3-methyl-7-phenylacetylamino-Δ³ -cephem-4-carboxylic acid, methyl ester and 2-methoxy-3-methyl-7-phenylacetylamino-Δ³-cephem-4-carboxylic acid, methyl ester Hydrogen sulfide is bubbled through a solution of 200 mg. of the product from part (a) in 15 ml. of 1% ethanol in chloroform for 1 hour, with care being made to exclude atmospheric moisture. The mixture is filtered through Celite, and the filtrate is evaporated to a residue. This residue is purified by thin layer chromatography on silica gel in the system CHCl₃— EtOAc (9:1) to give 2-ethoxy-3-methyl-7-phenylacetylamino-Δ³-cephem-4-carboxylic acid, methyl ester (19 mg.) and 2-methoxy-3-methyl-7-phenylacetylamino-Δ³-cephem-4-carboxylic acid, methyl ester (10 mg.). The 2 ethoxy ester has: pmr (DCCl₃) τ 8.78 (3H,t,O—C—CH₃), 7.87 (3H,s,C=C-CH₃), η6.4 (2H,q,—O—CH₂—C), 6.18 (3H,s,—COOCH₃), 5.15 (1H,d,J=0.5Hz,C-2), 4.95 (1H,d,J=5Hz, C-6), 4.17 (1H,q,J=5Hz,J=8Hz,C-7); ir (CHCl₃) 1780, 1730, and 1680 cm⁻¹; mass spectrum 390 (M⁺).

The 2-methoxy ester has: pmr (DCCl₃) τ 7.87 (3H,s,C= C—CH₃), 6.57 (3H,s,OCH₃), 6.18 (3H,s,—COOCH₃), 5.25 (1H,d, J=0.4Hz,C-2), 4.98 (1H,d,J=C-6), 4.17 (1H,q,J=Hz,J=8Hz, C-7); ir (CHCl₃) 1780, 1730, and 1680 cm⁻¹; mass spectrum 376 (M⁺).

EXAMPLE 3

2-Methoxy-3-methyl-7-phenylacetylamino-Δ³-cephem-4-carboxylic acid, diphenylmethyl ester a. Bis[[1-[1-[(diphenylmethoxy)carbonyl]-2-methyl-3,3-dimethoxy-1-propenyl]-3-[(phenylacetyl)amino]-4-oxo-2-azetidinyl]thio]mercury Following the procedure of example 1(a) but substituting an equivalent amount of 4-methylthio-7-phenylacetamido-3-methylΔ²-cephem-4-carboxylic acid, diphenylmethyl ester for the 2,2,2-trichloroethyl ester, one obtains the titled compound having the following spectral properties: pmr (DCCl₃) τ 4.45 (1H,d,J=5Hz,C-2), 4.75, 4.87 (1H,q,J=5Hz,J=8Hz,C-3), 5.03

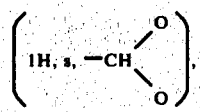

6.63 (3H,s,—OCH₃) 6.67 (3H,s,—OCH₃), ir (CHCl₃, cm⁻¹) 1770, 1720, 1680.

b. 2-Methoxy-3-methyl-7-phenylacetylamino-Δ³-cephem-4-carboxylic acid, diphenylmethyl ester Following the procedure of example 1 (b) but employing an equivalent amount of the mercury compound from part (a), one obtains the titled compound.

EXAMPLES 4–12

Following the procedure of example 1 (a) but employing either the Δ²-cephem or Δ³-cephem starting material shown in Col. I and the alcohol shown in Col. II one obtains the mercury compound shown in Col. III. The compound of Col. III can then be reacted as taught in example 1 (b) to yield the 2-alkoxy cephalosporin.

Col. I

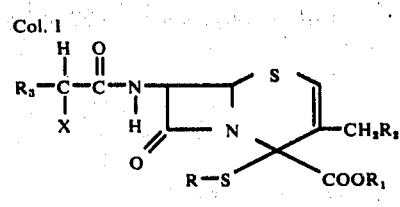

or

-continued

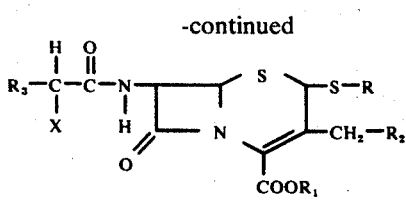

Col. II
HO—R₅

Col. III

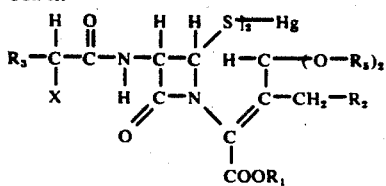

vacuo to a residue which is chromatographed on 400 g. of silica gel packed in CHCl₃. Elution with CHCl₃ provides 12.3 g. of the desired product as a residue.

b. 7-[(Triphenylmethyl)amino]-3-[(acetyloxy)methyl]-4-methylthio—Δ²-cephem-4-carboxylic, t-butyl ester To a stirred solution of the product from part (a) (5 mmol.) in 30 ml. of dry dimethoxyethane at −10° C under nitrogen is added 5 mmol. of potassium t-butoxide. The mixture is stirred for 2 minutes, and then methyl methanethiolsulfonate (5 mmol.) in 3 ml. of dimethoxyethane is added. The mixture is stirred at 0° for 1 hour and poured into pH 6.6 buffer—CHCl₃—ice. The CHCl₃ extract is washed with saturated NaCl, dried (Na₂SO₄), and evaporated to a residue, which is purified by dry column chromatography on a column of silica gel (2 inches × 24 inches) with CHCl₃ as a solvent, to give 1.89 g. of the desired product as a foam having:

| Ex. | R₃ | X | R | R₁ | R₂ | R₅ |
|---|---|---|---|---|---|---|
| 4 | —C₆H₅— | —O—C(=O)—CHCl₂ | —C₂H₅ | —CH₂CCl₃ | —O—C(=O)—CH₃ | —CH₃ |
| 5 | —C₆H₅— | —N(H)—C(=O)—O—C(CH₃)₃ | —CH₃ | —CH₂—C₆H₄—OCH₃ | —H | —i-C₃H₇ |
| 6 | cyclohexyl | —N(H)—C(=O)—O—CH₂—C₆H₄—OCH₃ | —CH₃ | —C(CH₃)₃ | —H | —n-C₄H₉ |
| 7 | —C₆H₅— | —H | C₆H₅ | —CH₂—C₆H₄—NO₂ | —O—C(=O)—CH₃ | —t-C₄H₉ |
| 8 | thienyl | —H | —CH₃ | —CH₃ | —H | —C₂H₅ |
| 9 | —C₆H₅—O— | —H | C₆H₅ | —C(CH₃)₃ | —O—C(=O)—CH₃ | —CH₃ |
| 10 | H₃C—C₆H₄— | —N(H)—C(=O)—O—C(CH₃)₃ | —CH₃ | —CH₂CCl₃ | —H | —CH₃ |
| 11 | 3,5-dichlorophenyl | —H | —C₂H₅ | —CH(C₆H₅)₂ | —O—C(=O)—CH₃ | —CH₃ |
| 12 | C₆H₅ | —H | —CH₃ | —C(CH₃)₃ | —H | —CH₃ |

EXAMPLE 13

3-[(Acetyloxy)methyl]-2-methoxy-7-phenylacetylamino-Δ³-cephem 4-carboxylic acid, t-butyl ester a. 7-[(Triphenylmethyl)amino]-3-[(acetyloxy)methyl]-Δ³-cephem-4-carboxylic acid, t-butyl ester A mixture of 7-amino cephalosporanic acid, t-butyl ester (30 mmol.), triphenylmethyl chloride (30 mmol.), and N,N-diisopropylethylamine (30 mmol.) in 150 ml. of dry CH₂Cl₂ is stirred at 25° under nitrogen for 4 hours. The reaction mixture is washed successively with water, dilute HCl at pH 2.0, and water. The CH₂Cl₂ layer is dried (Na₂SO₄) and evaporated in pmr (DCCl₃) τ 8.57 (9H,s,t-butyl), 7.98, 7.92 (two 3H singlets,SCH₃,OAc), 6.97 (1H, broad d,N-H), 5.52 (1H,d,J=4Hz,C-6), 5.38 (1H,q,J=4Hz,J=9Hz, C-7), 5.20 (2H,broad s,C-3 methylene), 3.43 (1H,broad s,J~0.5 Hz, C-2), and 2.67 (15H,m,aromatics).

c. Bis[[1-[(1,1-dimethylethoxy)carbonyl]-2-[(acetyloxy)methyl]-3,3-dimethoxy-1-propenyl]-3-[(triphenylmethyl)amino]-4-oxo-2-azetidinyl]thio]mercury Following the procedure of example 1 (a) but substituting an equivalent amount of the product part (b) for the 4-methylthio-7-phenylacetamido-3-methyl-Δ² -cephem-4-carboxylic acid, 2,2,2-dichloroethyl ester, one obtains the titled compound having the following spectral properties: pmr (DCCl₃) τ 4.73 (1H,d,J=5Hz,C-2), 5.32, 5.42 (1H,q,J=5Hz,J=8Hz,C-3),

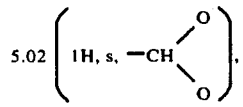

6.58 (3H,s,—OCH₃), 6.80 (3H,s,—OCH₃); ir (CHCl₃, cm⁻¹) 1760, 1730, 1720(sh).

d. 3-[(Acetyloxy)methyl]-2-methoxy-7-[(triphenylmethyl)amino]-Δ³-cephem-4-carboxylic acid, t-butyl ester Hydrogen sulfide is bubbled through a suspension of the mercury product from part (c) in dry dichloromethane, with care being taken to avoid atmospheric moisture at 25° C. The reaction mixture is filtered through Celite, and the filtrate is evaporated to a residue. The residue is purified by thin layer chromatography on silica gel to yield the titled compound.

e. 3-[(Acetyloxy)methyl]-7-amino-2-methoxy-Δ³-cephem-4-carboxylic acid, t-butyl ester A solution of 0.5 mmol. of the product from part (d) and 0.1 ml of concentrated hydrochloric acid in 10 ml. of acetone is stirred at 25° under nitrogen for 3 hours. The solvent is removed in vacuo, and the residue is treated with acetone and ether to give the hydrochloride salt of 3-[(acetyloxy)-methyl]-7-amino-2-methoxy-Δ³-cephem-4-carboxylic acid, t-butyl ester as a solid. The solid is suspended in chloroform-water, and the pH is adjusted to 7.5 with aqueous sodium bicarbonate. The chloroform layer is washed with water, dried (Na₂SO₄), and evaporated to give the titled compound as a residue.

f. 3-[(Acetyloxy)methyl]-2-methoxy-7-phenylacetylamino-Δ³-cephem-4-carboxylic acid, t-butyl ester The product from part (e) is acylated with phenylacetylchloride according to the procedure of Netherlands Pat. No. 7,308,544 to yield the titled compound.

EXAMPLE 14

Bis[[1-[1,1-dimethylethoxy)carbonyl]-2-[(acetyloxy)-methyl]-3,3-dimethoxy-1-propenyl]-3-[(triphenylmethyl)amino]-4-oxo-2-azetidinyl]thio]mercury The compound prepared in example 13 (c) can also be prepared by the following method.

a. 3-[Acetyloxy)methyl]-2-methylthio-7-[(triphenylmethyl)-amino]-Δ³-cephem-4-carboxylic acid, t-butyl ester To a stirred solution of 308 mg. (0.5 mmol.) of 3-[(acetyloxy)methyl]-4-methylthio-7-[(triphenylmethyl)amino]-Δ²-cephem-4-carboxylic acid, t-butyl ester from example 13 (b) in 8 ml. of dry dimethoxyethane under nitrogen is added 160 mg. (0.5 mmol.) of mercuric acetate. The mixture is stirred at room temperature for 1 hour and the solvent is removed in vacuo. The residue is treated with benzene and water, dried (Na₂. SO₄), and evaporated to yield 309 mg. of a residue. The residue is purified by chromatography on two 20 × 40 cm. × 1 mm. PQIF plates in the system chloroform-hexane (4:1) to yield the titled compound.

b. Bis[[1-[(1,1-dimethylethoxy)carbonyl]-2-[(acetyloxy)methyl-3,3-dimethoxy-1-propenyl]-3-[(triphenylmethyl)amino]-4-oxo-2-azetidinyl]thio]mercury To a stirred solution of 0.04 mmol. of the product form part (a) in 4 ml. of dry methanol under nitrogen is added (0.04 mmol.) of mercuric acetate. The mixture is stirred for 1 hour at 25°, and then the solvent is removed in vacuo. The residue is treated with benzene and water, and the benzene layer is washed with water four times, dried (Na₂SO₄) and evaporated to a second residue (22 mg.). This residue is purified by thin layer chromatography on silica gel in the system chloroform-hexane (4:1) to give the titled compound as an amorphous solid (10 mg.).

EXAMPLE 15

2-Methoxy-3-methyl-7-phenylacetylamino-Δ³-cephem-4-carboxylic acid,2,2,2-trichloroethyl ester a. 3-Methyl-7-triphenylmethylamino-Δ³-cephem-4-carboxylic acid, 2,2,2-trichloroethyl ester and corresponding Δ²-cephem isomer A mixture of 7-amino desacetoxycephalosporanic acid 2,2,2-trichloroethyl ester (0.039 mol.), triphenylmethyl chloride (0.039 mol.), and triethylamine (0.039 mol.) in 150 ml. of dry CH₂Cl₂ is stirred at 25° under nitrogen for 4 hours. The mixture is washed with water, dried (Na₂SO₄), and evaporated in vacuo to give the desired product as a residue (27.6 g.). Purification of this residue by dry column chromatography on four 2 inches × 24 inch columns using CHCl₃ provides, from inches 8 to 20, the desired product (18.9 g.) as a mixture of Δ² and Δ³-cephem isomers.

b. 3-Methyl-4-methylthio-7-triphenylmethylamino-Δ²-cephem-4-carboxylic acid,2,2,2-trichloroethyl ester To a stirred solution of the product from part (a) (31.9 g., 0.0545 mol.) in 200 ml. of dry dimethoxyethane at −10° under N₂ is added potassium t-butoxide (6.14 g., 0.0545 mol.). The mixture is stirred for 3 minutes, and then methyl methanethiosulfonate (6.87 ., 0.0545 mol.) in 30 ml. of dimethoxyethane is added dropwise but rapidly. Stirring is continued at −10° for 1 hour, and the dark red-brown mixture is poured into pH 6.6 buffer-ice-CHCl₃. Repeated extraction with CHCl₃ provides after drying (Na₂SO₄), and evaporation of the CHCl₃ in vacuo the desired product as a foam (33.5 g., 80% pure as determined by pmr spectroscopy), having pmr (DCCl₃) τ 8.07 (3H,d,J=0.5Hz,C-3 methyl), 7.90 (3H,s,SCH₃), 6.93 (1H,brod, N—H), 5.50 (2H,broad s,C-6 and C-7), 5.27 (2H,s,—CH₂—CCl₃), 3.85 (1H,d,J=0.5Hz,C-2), 2.6 (15H,m, aromatics).

c. Bis[[1-[1-[(2,2,2-trichloroethoxy)carbonyl]-2-methyl-3,3-dimethoxy-1-propenyl]-3-[(triphenylmethyl)amino]-4-oxo-2-azetidinyl]thio]mercury Following the procedure of example 1 (a) but substituting an equivalent amount of the product from part (b) for the 4-methylthio-7-phenylacetylamino-3-methyl-Δ²-cephem-4-carboxylic acid,2,2,2-trichloroethyl ester, one obtains the titled compound having the following spectral properties: pmr (DCCl₃) τ 3.16 (1H,broad d,C-2), ~5.2 (1H,q,J=5Hz,C-3),

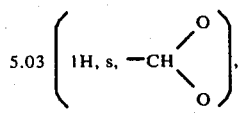

6.57 (3H,s,—OCH$_3$), 6.70 (3H,s,—OCH$_3$); ir (CHCl$_3$, cm$^1$) 1765 (broad).

d. 3-Methyl-2-methoxy-7-[(triphenylmethyl)amino]-Δ$^3$-cephem-4-carboxylic acid, 2,2,2-trichloroethyl ester Treating the product from part (c) with hydrogen sulfide according to the procedure of example 13 (d) yields the titled compound.

e. 7-Amino-2-methoxy-3-methyl-Δ$^3$-cephem-4-carboxylic acid, 2,2,2-trichloroethyl ester Treating the product from part (d) with hydrochloric acid according to the procedure of example 13 (e) yields the titled compound.

f. 2-Methoxy-3-methyl-7-phenylacetylamino-Δ$^3$-cephem-4-carboxylic acid, 2,2,2-trichloroethyl ester Acylating the product from part (e) with phenylacetylchloride according to the procedure of Netherlands Pat. No. 7,308,544 yields the titled compound.

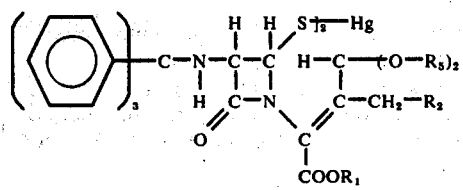

Col. IV

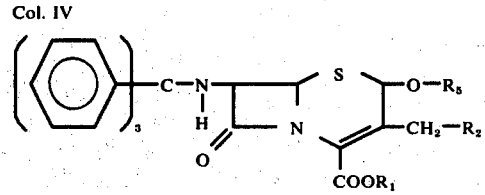

| Ex. | R | R$_1$ | R$_2$ | R$_5$ |
|---|---|---|---|---|
| 16 | C$_6$H$_5$– | —CH$_3$ | —H | —C$_2$H$_5$ |
| 17 | —C$_2$H$_5$ | —CH$_2$–C$_6$H$_4$–OCH$_3$ | —O—C(O)—CH$_3$ | —n-C$_3$H$_7$ |
| 18 | —CH$_3$ | —CH$_2$–C$_6$H$_4$–NO$_2$ | —H | —t-C$_4$H$_9$ |
| 19 | —CH$_3$ | —CH(C$_6$H$_5$)$_2$ | —O—C(O)—CH$_3$ | —CH$_3$ |
| 20 | —C$_2$H$_5$ | —C(CH$_3$)$_3$ | —H | —n-C$_4$H$_9$ |

EXAMPLES 16–20

Following the procedures of examples 13 or 14 but employing either the Δ$^2$-cephem or Δ$^3$-cephem starting material shown in Col. I and the alcohol shown in Col. II one obtains the mercury compound shown in Col. III. The compound of Col. III can then be reacted with hydrogen sulfide according to the procedure of example 13(d) to yield the compound shown in Col. IV. The compound of Col. IV can then be converted to the corresponding 7-acyl-2-alkoxy-cephalosporin by the procedure of examples 13(e) and (f).

Col. I

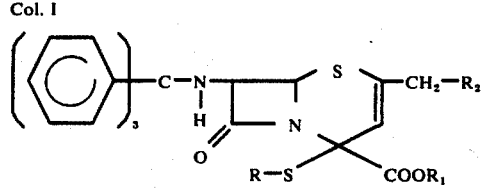

or

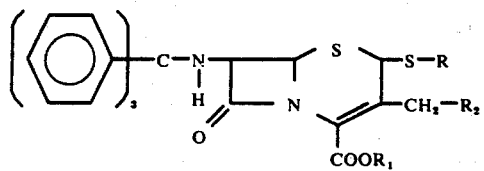

Col. II
HO—R$_5$

Col. III

EXAMPLE 21

2-Methoxy-3-methyl-7-phenylacetylamino-Δ$^3$-cephem-4-carboxylic acid, t-butyl ester a. Bis[[1-[1-[(1,1-dimethylethoxy)carbonyl[-2-methyl-3,3-dimethyl-1-propenyl]-3-phthalimido-4-oxo-2-azetidinyl]thio]mercury Following the procedure of example 1 (a) but substituting an equivalent amount of 4-methylthio-7-phthalimido-3-methyl-Δ$^2$-cephem-4-carboxylic acid, t-butyl ester for the 4-methylthio-7-phenylacetamido-3-methyl-Δ$^2$-cephem-4-carboxylic acid,2,2,2-trichloroethyl ester, one obtains the titled compound having the following spectral properties: pmr (DCCl$_3$) τ 4.17 (1H,d, J=5Hz,C-2), 4.37 (1H,d,J=5Hz,C-3),

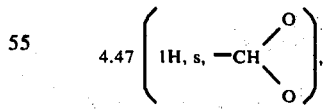

6.42 (3H,s,—OCH$_3$), 6.50 (3H,s,—OCH$_3$).

b. 2-Methoxy-3-methyl-7-phthalimido-Δ$^3$-cephem-4-carboxylic acid, t-butyl ester The product from part (a) is treated with hydrogen sulfide according to the procedure of example 13(d) to yield the titled compound.

c. 2-Methoxy-3-methyl-7-amino-Δ$^3$-cephem-4-carboxylic acid, t-butyl ester

The product from part (b) is treated to cleave the phthalimide group according to the procedure of Kukolja et al., Jour. Amer. Chem. Soc., Vol. 97, p. 5582–5583.

d. 2-Methoxy-3-methyl-7-phenylacetylamino-Δ$^3$-cephem-4-carboxylic acid, t-butyl ester The product from part (c) is acylated with phenylacetylchloride according to the procedure of Netherlands Pat. No. 7,308,544 to yield the titled compound.

EXAMPLES 22–26

Following the procedure of example 21 but employing either the Δ$^2$-cephem or Δ$^3$-cephem starting material shown in Col. I and the alcohol shown in Col. II one obtains the mercury compound shown in Col. III. The compound of Col. III can then be treated as in example 21 (b), (c) and (d) to yield various 7-acyl-2-alkoxy-cephalosporins.

Col. I

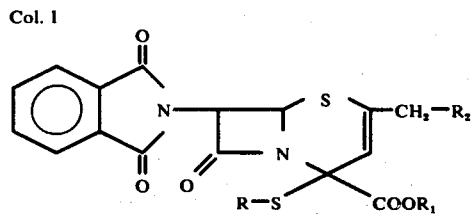

or

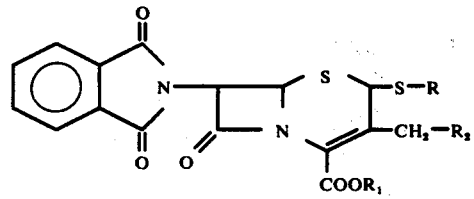

Col. II
HO—R$_5$

Col. III

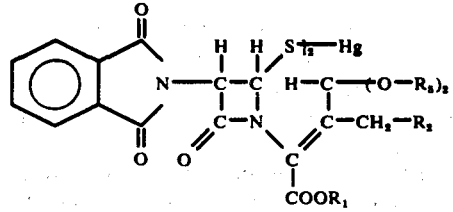

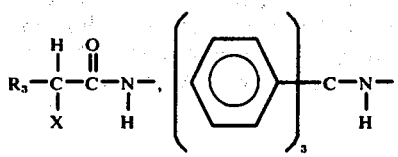

wherein R$_1$ is lower alkyl, diphenylmethyl, 2,2,2-trichloroethyl, p-methoxybenzyl, or p-nitrobenzyl; R$_2$ is hydrogen or acetoxy; R$_5$ is lower alkyl; and R$_4$ is

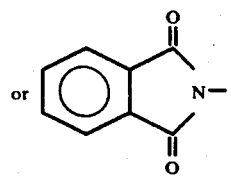

wherein X is hydrogen, protected amino of the formula

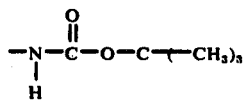

or  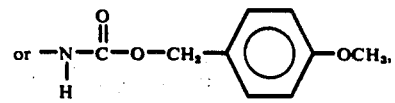

or protected hydroxy of the formula

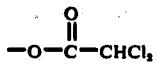

and R$_3$ is lower alkyl, cycloalkyl of 3 to 7 carbons,

| Ex. | R | R$_1$ | R$_2$ | R$_5$ |
|---|---|---|---|---|
| 22 | —C$_6$H$_5$— | —CH$_3$ | —O—C(O)—CH$_3$ | —CH$_3$ |
| 23 | —CH$_3$ | —CH(C$_6$H$_5$)$_2$ | —H | —C$_2$H$_5$ |
| 24 | —CH$_3$ | —CH$_2$—C$_6$H$_4$—NO$_2$ | —O—C(O)—CH$_3$ | —i-C$_3$H$_7$ |
| 25 | —C$_2$H$_5$ | —CH$_2$—C$_6$H$_4$—OCH$_3$ | —H | —n-C$_4$H$_9$ |
| 26 | —CH$_3$ | —CH$_2$—CCl$_3$ | —O—C(O)—CH$_3$ | —CH$_3$ |

What is claimed is:
1. A compound of the formula:

cycloalkenyl of 3 to 7 carbons, cycloalkadienyl of 6 to 7 carbons, phenyl, phenoxy, phenyllower alkyl, substituted phenyl wherein said substituent is one or two members selected from the group consisting of lower alkyl, lower alkoxy, and halogen, or heterocyclic wherein said heterocyclic is attached by way of an available carbon atom and is unsubstituted or substituted at an available carbon atom by a lower alkyl or halogen group and is selected from the group consisting of thienyl, furyl, pyrryl, pyridyl, thiazolyl, isothiazolyl, oxazolyl, isoxazolyl, thiadiazolyl and tetrazolyl provided that X is protected amino or protected hydroxy only when $R_3$ is phenyl, substituted phenyl or cycloalkadienyl.

2. The compound of claim 1 wherein $R_4$ is

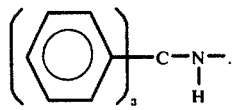

3. The compound of claim 2 wherein $R_5$ is methyl.
4. The compound of claim 1 wherein $R_4$ is

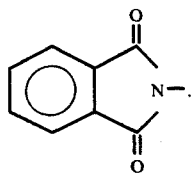

5. The compound of claim 4 wherein $R_5$ is methyl.
6. The compound of claim 1 wherein $R_4$ is

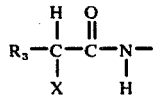

and $R_3$ is phenyl, phenoxy, or 2-thienyl; X is hydrogen,

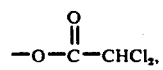

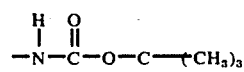

or

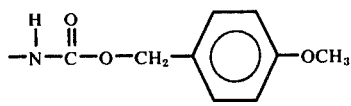

provided that X is

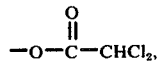

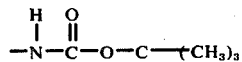

or

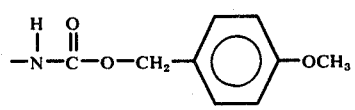

only when $R_3$ is phenyl.
7. The compound of claim 6 wherein $R_5$ is methyl.
8. The compound of claim 7 wherein X is hydrogen and $R_3$ is phenyl.
9. A process for preparing the compound of claim 1 which comprises treating a compound selected from the group consisting of

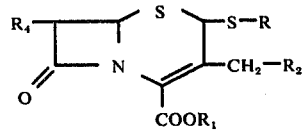

and

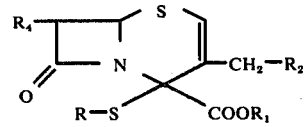

wherein $R_1$, $R_2$ and $R_4$ are as defined in claim 1 and R is lower alkyl or phenyl, with mercuric acetate and an alcohol of the formula $R_5$—OH wherein $R_5$ is as defined in claim 1 in the presence of an inert organic solvent or where the alcohol also functions as the solvent at a temperature of from about 0° C to about 80° C for from about 5 minutes to about 2 hours.

* * * * *

UNITED STATES PATENT AND TRADEMARK OFFICE
CERTIFICATE OF CORRECTION

PATENT NO. : 4,029,645
DATED : June 14, 1977
INVENTOR(S) : William A. Slusarchyk, Christopher M. Cimarusti It is certified that error appears in the above-identified patent and that said Letters Patent are hereby corrected as shown below:

Col. 1, line 8, "spry" should read -- Spry --.
Col. 2, line 18, "pG" should read -- pH --.
Col. 2, line 37, "4chlorophenyl," should read -- 4-methylphenyl --.
Col. 4, line 66, "German Offenlegungsschrift" should read
    -- German Offenlegungsschrifts --.
Col. 6, line 45, "Bis[[1-[(2,2,2-" should read --Bis[[1-[1-[(2,2,2-
Col. 6, line 61, "$\Delta$ 4.27" should read -- $\tau$ 4.27 --.
Col. 7, line 34, "$(M^{+)}$" should read -- $(M^+)$. --.
Col. 7, line 25, (1H,q,J=5Hz,J=9H,C-7);" should read
    -- (1H,q,J=5Hz,J=9Hz,C-7); --
Col. 7, line 59, "2Ethoxy" should read -- 2-Ethoxy --.
Col. 8, line 7, "$\eta$6" should read -- $\nu$6 --.
Col. 8, line 15, "(1H,d J=0.4Hz, C-2)," should read --(1H,d J=0.5Hz, C-2), --.
Col. 8, line 16, "(1H,d,J=C-6)," should read -- (1H,d,J=5Hz,C-6), --
Col. 9, line 64, "mmol).," should read -- mmol.), --.
Col. 11, line 46, "Bis[[1-[1,1-" should read -- Bis[[1-[1-[(1,1- --.
Col. 11, line 67, "Bis[[1-[(1,1-" should read --Bis[[1-[1-[(1,1--.
Col. 12, line 39, "(6.87" should read -- (6.87g --.
Col. 12, line 48, "(1H,brod," should read --(1H,broad, --.
Col. 13, line 2, "$cm^1$)" should read -- $cm^{-1}$) --.

UNITED STATES PATENT AND TRADEMARK OFFICE
CERTIFICATE OF CORRECTION

PATENT NO. : 4,029,645
DATED : June 14, 1977
INVENTOR(S) : William A. Slusarchyk, Christopher M. Cimarusti It is certified that error appears in the above-identified patent and that said Letters Patent are hereby corrected as shown below:

Col. 13, lines 51-58, the circle which appears in the following formula should be completely closed:

Col. 1

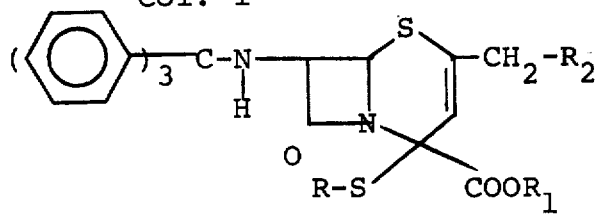

Col. 14, line 42, "carbonyl[-2-" should read --carbonyl]-2- --.

Col. 15, lines 20-26,

" Col. 1 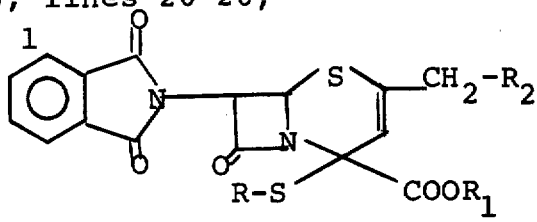 " should read: (see next page)

UNITED STATES PATENT AND TRADEMARK OFFICE
CERTIFICATE OF CORRECTION

PATENT NO. : 4,029,645
DATED : June 14, 1977
INVENTOR(S) : William A. Slusarchyk, Christopher M. Cimarusti It is certified that error appears in the above-identified patent and that said Letters Patent are hereby corrected as shown below:

-- Col. 1

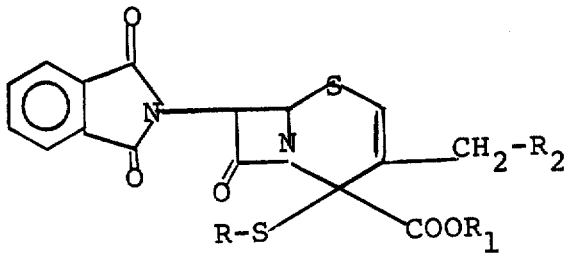

--.

Signed and Sealed this

Eighteenth Day of October 1977

[SEAL]

Attest:

RUTH C. MASON
Attesting Officer

LUTRELLE F. PARKER
Acting Commissioner of Patents and Trademarks